US006641842B2

(12) United States Patent
Laridon et al.

(10) Patent No.: US 6,641,842 B2
(45) Date of Patent: Nov. 4, 2003

(54) THERMOPLASTIC ARTICLES EXHIBITING HIGH SURFACE-AVAILABLE SILVER

(75) Inventors: Erik Laridon, Heverlee (BE); Geoffrey Haas, Spartanburg, SC (US); Robert Dankel, Taylors, SC (US)

(73) Assignee: Milliken & Company, Spartanburg, SC (US)

( * ) Notice: Subject to any disclaimer, the term of this patent is extended or adjusted under 35 U.S.C. 154(b) by 9 days.

(21) Appl. No.: 10/015,872

(22) Filed: Dec. 12, 2001

(65) Prior Publication Data

US 2003/0113378 A1 Jun. 19, 2003

(51) Int. Cl.[7] ............................. A61K 9/14; A61F 13/00
(52) U.S. Cl. ...................... 424/486; 424/484; 424/485; 424/422
(58) Field of Search ................................ 424/486, 484, 424/485, 422

(56) References Cited

U.S. PATENT DOCUMENTS

| | | | |
|---|---|---|---|
| 4,938,955 A | | 7/1990 | Niira et al. .................... 424/79 |
| 5,405,644 A | | 4/1995 | Ohsumi et al. ............. 427/2.31 |
| 5,556,699 A | * | 9/1996 | Niira et al. ................. 428/323 |
| 5,750,609 A | | 5/1998 | Nosu et al. ................. 524/413 |
| 6,454,813 B1 | * | 9/2002 | Chan ......................... 8/115.51 |
| 6,544,621 B1 | * | 4/2003 | Schuette et al. ............. 428/97 |

FOREIGN PATENT DOCUMENTS

JP 2000119435 A * 4/2000

* cited by examiner

Primary Examiner—Thurman K. Page
Assistant Examiner—Rachel M. Bennett
(74) Attorney, Agent, or Firm—Terry T. Moyer; William S. Parks

(57) ABSTRACT

Improvements in increasing the amount of surface-available silver in thermoplastic articles comprising certain silver-containing antimicrobial agents. Such an invention requires the incorporation of a sufficient amount of a carboxylic acid salt within the thermoplastic article simultaneously with the necessary silver-containing antimicrobial agent. Certain carboxylic acid salts are standard acid scavengers and lubricants for certain thermoplastic applications; however, the amounts required within this inventive thermoplastic article are in excess of that commonly added within such articles, and the types of acid scavengers possibly added within such target thermoplastic articles are preferably neutralized hydrotalcite compounds, thereby permitting the carboxylic acid salt to function in the inventive manner. Surprisingly, such a high amount of such standard salts, as well as potentially other non-standard salts, present within the target thermoplastic cause the release of greater amounts of silver to the target article's surface, thereby permitting a greater degree of antimicrobial activity, among other potential benefits for such an increase in surface-available silver. Methods of producing such inventive thermoplastics are also encompassed within this invention.

2 Claims, No Drawings

THERMOPLASTIC ARTICLES EXHIBITING HIGH SURFACE-AVAILABLE SILVER

FIELD OF THE INVENTION

This invention relates to improvements in increasing the amount of surface-available silver in thermoplastic articles comprising certain silver-containing antimicrobial agents. Such an invention requires the incorporation of a sufficient amount of a carboxylic acid salt within the thermoplastic article simultaneously with the necessary silver-containing antimicrobial agent. Certain carboxylic acid salts are standard acid scavengers and lubricants for certain thermoplastic applications; however, the amounts required within this inventive thermoplastic article are in excess of that commonly added within such articles, and the types of acid scavengers possibly added within such target thermoplastic articles are preferably neutralized hydrotalcite compounds, thereby permitting the carboxylic acid salt to function in the inventive manner. Surprisingly, such a high amount of such standard salts, as well as potentially other non-standard salts, present within the target thermoplastic cause the release of greater amounts of silver to the target article's surface, thereby permitting a greater degree of antimicrobial activity, among other potential benefits for such an increase in surface-available silver. Methods of producing such inventive thermoplastics are also encompassed within this invention.

DISCUSSION OF THE PRIOR ART

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; Salmonella contamination causing sicknesses from undercooked and unwashed poultry food products; and illnesses and skin infections attributed to *Staphylococcus aureus*, yeast, and other unicellular organisms. With such an increased consumer interest in this area, manufacturers have begun introducing antimicrobial agents within various household products and articles.

Silver-containing inorganic microbiocides have recently been developed and utilized as antimicrobial agents on and within a plethora of different substrates and surfaces. In particular, such microbiocides have been adapted for incorporation within plastic compositions and fibers in order to provide household and consumer products which inherently exhibit antimicrobial characteristics. Although such silver-based agents provide suitable antimicrobial properties within thermoplastic articles, and other types of articles, there are certain limitations as to the potential antimicrobial efficacy of such thermoplastic articles. Such limitations are apparently due to relatively low amounts of surface-available silver within and/or on such thermoplastic articles. Without intending to be bound to any specific scientific theory, it is believed that such low surface-available amounts of silver are the result of the inability of a sufficient amount of the integrated silver compounds to migrate to the thermoplastic surface. Such a result is observed for standard thermoplastics comprising silver-containing antimicrobials. Thus, there exists a need to provide efficacious amounts of silver-containing antimicrobial agents within thermoplastic compositions that exhibit such heretofore unattainable high levels of surface-available silver compounds, thereby providing more effective antimicrobial activity, among other potential desirable characteristics as a result thereof.

Past plastic compositions and articles comprising silver-containing antimicrobial agents include U.S. Pat. No. 5,405,644 to Ohsumi et al., which includes the addition of certain triazoles, U.S. Pat. No. 4,938,955 to Niira, deceased et al. (also including benzotriazole stabilizers), U.S. Pat. No. 5,750,609 to Nosu et al., which discloses an ultraviolet protective agent for incorporation within a variety of compositions, such as films, fibers, cosmetics, and the like, comprising a zinc-based hydrotalcite which acts solely as an ultraviolet absorber. However, these particular methods and plastics have proven to be costly (with the high expense of benzotriazoles initially), particularly since relatively high concentrations of the expensive stabilizing compounds are required, and do not provide any appreciable increase of available silver on the surface of such articles. Also, as these stabilizers are not thermally stable, they introduce additional processing complications. As such, there is no teaching or fair suggestion within the prior art which pertains to the needed improvement in increasing the amounts of surface-available silver compounds on target thermoplastics.

DESCRIPTION OF THE INVENTION

It is thus an object of the invention to provide an increase in the amount of surface-available silver to actual thermoplastic articles (containers, plaques, films, fibers, and the like). A further object of the invention is to provide such an increase through the utilization of acceptable, commercially available, components for thermoplastic formulations. Another object of the invention is to provide a highly efficacious antimicrobial thermoplastic article. Yet another object of this invention is to provide a cost-effective method of increasing the amount of surface-available silver on such target inventive thermoplastic articles and thereby reducing the amount of active silver remaining within the target resin itself.

Accordingly, this invention encompasses a thermoplastic article comprising at least one silver-containing antimicrobial agent, optionally at least one acid scavenger compound, and from 0.1% to 1.25% by weight, preferably from about 0.2 to about 1.0%, more preferably from about 0.2 to about 0.5%, and most preferably about 0.3% by weight of at least one carboxylic acid salt component other than or in excess of said optional at least one acid scavenger compound. Furthermore, this invention also encompasses a method of forming a thermoplastic article comprising the steps of providing a thermoplastic polymer, introducing at least one silver-containing antimicrobial agent, optionally at least one acid scavenger compound, and from at least 0.1% to 1.25% by weight, preferably from about 0.2 to about 1.0%, more preferably from about 0.2 to about 0.5%, and most preferably about 0.3% by weight of at least one carboxylic acid salt component other than or in excess of said optional at least one acid scavenger compound, melting said resultant mixture of polymer, silver-containing antimicrobial agent, and at least one carboxylic acid salt, and cooling said molten mixture in a desired shaped thermoplastic article. Also, this invention encompasses a polyolefin article comprising at least one silver-containing antimicrobial agent and exhibiting a surface-available amount of silver of at least 0.25 micrograms of silver/square decimeter (or a styrenic thermoplastic article exhibiting an amount of at least 0.80 micrograms of silver/square decimeter in terms of surface-available silver) of said surface, as measured by a salt-extraction test for 24 hours at room temperature. Nowhere within the prior art has such a specific plastic article or method of making thereof been disclosed, utilized, or fairly suggested to produce a thermoplastic article with such desirable increased surface-available silver characteristics.

The term "surface-available silver" is intended to encompass the phenomenon of the detectable presence of available silver, either as metals or ions, on the target article's surface or, possibly from a distance very close to such surface but imbedded therein until extracted out with relative ease. Detection in this instance is accomplished through a particular method, as eluded to above, wherein the sample article is immersed within an extracting solution, such as, as one example, a mixed salt solution (in this instance a sodium-potassium-phosphate buffer solution) for at least twenty-four hours at room temperature. After such time, the extract solution is then analyzed through, for example, and without intended limitation, Inductive Coupled Plasma spectroscopy (hereinafter referred to as ICP) for the presence of silver therein which would have been removed from the target thermoplastic during the extraction process. The detection of such silver thus indicates the availability of silver at or near the article's surface and thus correlates to an increase in activity in relation to the availability of such silver in such a manner.

The closest art all involves the presence of silver-containing antimicrobial agents within thermoplastics, but do not concern the need for or possibility of increasing such desirable surface-available silver compounds. Such prior art is discussed above.

Any plastic in which a silver-based antimicrobial agent may be properly incorporated can be utilized in this invention. For instance, and without intending any limitations therein, polyolefins, such as polyethylene, polypropylene, and polybutylene, styrenics, such as polystyrene, ABS, and the like, and polyesters, such as polyethylene terephthalate, may be utilized within this invention. Preferably, the plastic is a thermoplastic that can be molded into different shapes and sizes upon extrusion a molding with the silver-containing antimicrobial and the required excess amount of carboxylic acid salts. Thus, polyolefins, particularly polypropylene, and styrenics, particularly polystyrene, are preferred. Furthermore, such plastics preferably may be colored to provide other aesthetic features for the end user. Thus, the plastic may also comprise colorants, such as, for example, poly(oxyalkylenated) colorants, pigments, dyes, and the like, too. Other additives may also be present, including antistatic agents, brightening compounds, nucleating agents, clarifying agents, lubricants, flame retardants, antioxidants, UV stabilizers, fillers, and the like.

The preferred silver-containing antimicrobial is an inorganic silver-containing compound, including, without limitation, inorganic compounds such as silver zirconium phosphates available from Milliken & Company under the tradename ALPHASAN® RC-2000, RC-5000, and RC-7000, although any silver-containing inorganic antimicrobial agent may also be utilized within the inventive plastic article (for instance, as mere examples, a silver substituted zeolite available from Shingawa under the tradename ZEOMIC®, and silver-containing glasses, such as IONPURE® from Ishizuka Glass under the tradename IONPURE®, as well as AMP® T558 and MICROFREE®, both available from DuPont, as well as JMAC®, available from Johnson Mathey). Generally, such an antimicrobial is added in an amount of from about 0.01 to 10% by total weight of the target plastic composition; more preferably from about 0.05 to about 2.0%; and most preferably from about 0.5 to about 2.0%.

The carboxylic acid salt may be any such salt based upon monovalent, bivalent, or trivalent metal ions and from $C_1-C_{40}$ in carbon chain length. Preferably, such at least one carboxylic acid salt is selected from the group consisting of at least one $C_1-C_{40}$ carboxylic acid compound neutralized by at least one cation selected from the group consisting of monovalent metal ions, bivalent ions, and trivalent metal ions. Such ions include, without limitation, monovalents such as alkali metals (e.g., sodium, potassium, lithium, and like) bivalents such as alkaline earth metals (e.g., calcium, barium, strontium, magnesium, cadmium, rubidium, and the like), zinc, tin (II), iron (II), such as aluminum, for example. It appears that the bi- and tri-valents provide the best overall thermoplastic article from both a surface-available silver compound standpoint and an aesthetic perspective because discoloration appears to be a greater problem with monovalents than for the others. However, such discoloration is greater for the larger-sized monovalent metal ions (e.g., sodium and potassium) for some undetermined reason. Although such compounds do appear to brown or yellow the target inventive resins to a certain extent, such colors may also be acceptable, or even desired, for certain reasons as well, thus the utilization of such carboxylic acid salts is not completely discouraged, and thus remains possible within the invention. Preferably, also, said carboxylic acid salt is preferably selected from the group consisting of alkali metal acetates, alkali metal stearates, alkaline earth metal acetates, alkaline earth metal stearates, zinc stearate, tin(II) stearate, aluminum stearate (as well as di- and tri-stearate), and any mixtures thereof (although other chain lengths, including myristates, behenates, oleates, palmitates, and the like, may also be utilized, these stearates and acetates are non-limiting preferred examples for this invention). Most preferred, though again, non-limiting, is calcium stearate, due to its advantages in processing as well as ultimate efficacy within the finished target thermoplastic article, as shown below. As noted above, the carboxylic acid salt should be added in amounts of from about 0.1% to 1.25% by weight, preferably from about 0.2 to about 1.0%, more preferably from about 0.2 to about 0.5%, and most preferably about 0.3% by weight of the total polymer component. Such amounts are in excess of any other acid scavenger compounds that are present within the target polymer itself (and preferably none of the carboxylic acid salts are utilized as acid scavengers in addition to this inventive purpose). In any event, such amounts are generally well in excess of standard additive amounts for acid scavenging carboxylic acid salts (such as calcium stearate, as one example) utilized within thermoplastic articles. Surprisingly, then, it has been found that such excess amounts of carboxylic acid salts are instrumental in providing the highly desirable increase in surface-available silver compounds on the target thermoplastic articles comprising silver-containing antimicrobial agents. It is not fully understood why such an addition of excess amount works in such a manner; however, the presence of too much carboxylic acid salt (e.g., greater than the maximum amount noted above, such as about 1.3% by weight of the total polymer component and above, as well as, in some circumstances, even amounts within the possible range of proportions noted above) exhibits a sharp reduction in such surface-available silver compounds and thus cannot function properly (and, in fact, results in an amount of such silver compounds well below that for a control of thermoplastic comprising only the silver-containing antimicrobial agent and no carboxylic acid salt at all). Again, such a selection criteria for the necessary carboxylic acid salt is highly unexpected to provide what is believed to provide a much-improved antimicrobial thermoplastic article ultimately.

As noted below, the basic procedures followed in producing the inventive antimicrobial plastic article comprise standard plastic formation techniques. There are two basic methods of incorporating additives (such as silver-containing antimicrobials and the necessary carboxylic acid salts, for example) within polymer articles. One method is to dry blend a mixture of polymer, additives, antimicrobials, and carboxylic acid salt; melting the dry mix into a molten formulation which is then eventually cooled and cut into pellets; the pellets are then introduced within an injection molding machine, or other similar type of processing equipment, and ultimately cooled into a shaped article. Alternatively, one may mix conventional resin pellets and a masterbatch concentrate containing the antimicrobial and carboxylic acid salt additives and molding in conventional molding equipment. The aforementioned molding steps may be performed preferably with injection molding equipment; however, other plastic-forming operations may also be utilized such as, and without limitation, blow molding, fiber extrusion, film formation, compression molding, rotational molding, and the like. These alternative plastic article-forming operations would be well understood and appreciated by one of ordinary skill in this art. The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article. For styrenics, such a procedure generally entails the utilization of pelletized polymers including antioxidant, lubricant, and the like, additives previously incorporated therein, to which powdered antimicrobial and carboxylic acid salt components may then be mixed therewith. The resultant solid pellets can then be melted by a heated screw during melting and mixing of the molten components prior to extrusion, or other process step.

Other additives may also be used in the composition of the present invention, provided they do not interfere with the primary benefits of the invention. It may even be advantageous to premix these additives or similar structures with the silver-containing antimicrobial agent(s) and carboxylic acid salts in order to reduce their melting points and thereby enhance dispersion and distribution during melt processing. Such additives are well known to those skilled in the art, and include nucleating agents, plasticizers, lubricants, catalyst neutralizers, antioxidants, light stabilizers, colorants, acid scavengers, and the like. Some of these additives may provide further beneficial property enhancements, including improved aesthetics, easier processing, and improved stability to processing or end use conditions.

In particular, it is contemplated that the acid scavengers utilized herein are primarily not the same carboxylic acid salts as needed for the desired increase in surface-available silver on the target thermoplastic article. Thus, as one example, dihydrotalcite types (such as, primarily, through without limitation, DHT4-A from Kyowa Chemical Industry Co., Ltd.) are preferred for this purpose, thereby permitting any carboxylic acid salts to be utilized primarily for the aforementioned inventive silver-generating purpose.

The compositions of the present invention are suitable as additives to improve the antimicrobial efficacy, and any other characteristic for which surface-available silver is highly desirable, of packaging materials and container materials for cosmetics, food-stuffs, films, thermoformed articles (drinking cups, for example), thick-walled storage containers, medical applications (syringes, intravenous bags, gloves, and the like), food processing equipment (conveyors belts, and the like) and other similar and typical end-uses for which antimicrobial thermoplastics are highly desired, particularly because they provide excellent efficacy for such film, sheet, or other similar fabricated thermoplastic articles without deleterious affecting such an article's physical properties.

DESCRIPTION OF THE PREFERRED EMBODIMENT

The following examples are indicative of the preferred embodiment of this invention:
Antimicrobial Thermoplastic Article Production Thermoplastic articles were produced in accordance with the different compositions listed below (all such compositions weighed 1000 g prior to molding):

| HOMOPOLYMER POLYPROPYLENE COMPOSITION TABLE | |
|---|---|
| Component | Amount |
| Polypropylene homopolymer (Himont Profax ® 6301 NT, from Basell) | to 1000 g |
| Irganox ® B215, Antioxidant (from Ciba Specialty Chemicals) | 1500 ppm |
| DHT4-A, Acid Scavenger | 400 ppm |
| Silver-Containing Antimicrobial Agent (type noted below) | as noted below |
| Carboxylic Acid Salt (type noted below) | as noted below |

| HIGH DENSITY POLYETHYLENE COMPOSITION TABLE | |
|---|---|
| Component | Amount |
| High Density Polyethylene (DOW ® 8454N, commercial resin comprising a pre-produced formulation of polymer with antioxidants and acid scavengers) | to 1000 g |
| Silver-Containing Antimicrobial Agent (type noted below) | as noted below |
| Carboxylic Acid Salt (type noted below) | as noted below |

| LINEAR LOW DENSITY POLYETHYLENE COMPOSITION TABLE | |
|---|---|
| Component | Amount |
| Linear Low Density Polyethylene (DOWLEX ® 2552-E, commercial resin comprising a pre-produced formulation of polymer with antioxidants and acid scavengers) | to 1000 g |
| Silver-Containing Antimicrobial Agent (type noted below) | as noted below |
| Carboxylic Acid Salt (type noted below) | as noted below |

| POLYSTYRENE COMPOSITION TABLE | |
|---|---|
| Component | Amount |
| Polystyrene (DOW Styron ® 660-71, commercial resin comprising a pre-produced formulation of polymer with antioxidants and acid scavengers) | to 1000 g |
| Silver-Containing Antimicrobial Agent (type noted below) | as noted below |
| Carboxylic Acid Salt (type noted below) | as noted below |

The polypropylene articles were produced by first mixing the polypropylene fluff together with the other components as listed to form a solid mixture of all such components. The solid mixture was then introduced within a hopper for further melting on a standard heated screw extruder. The molten mixture thus mixed thoroughly, and pelletized before being finally molded into a desired shape, into which they were then cooled into desired configurations for further use, in this case as plaques.

The polyethylene and polystyrene articles were all produced by taking pre-produced pellets of the (commercially available) polymer with other additives already provided, except the necessary silver-containing antimicrobial agents and the accompanying carboxylic acid salts. These powdered components were then mixed prior to melting with the aforementioned pellets to form a similar solid mixture for further melt extruding and mixing via a heated screw extruder. The molded articles were also plaques that were then cooled sufficiently to form the desired solid articles for the purpose of further testing and analysis.

Of course, although screw extruding and molding techniques were followed to form plaques in this preferred instance, it should be evident that any techniques standard within the thermoplastic article production industry to form any solid articles of such broadly defined polymeric articles may be followed as well.

The specific compositions produced conform with the particulars set forth in the Table below in terms of type of polymer (from above)(PP indicates from the Homopolymer Polypropylene Compositions Table, HDPE from the High Density Polyethylene Table, LLDPE from the Linear Low Density Polyethylene Table, and PS from the Polystyrene Table), type of silver-containing antimicrobial agent (generally, and non-limiting, in an amount of 10000 ppm, or about 1% by weight of the total polymer content of RC-2000 and RC-5000 are ALPHASAN® silver-containing compounds, and ZEOMIC®, is a zeolite-based compound, as noted above), and type of carboxylic acid salt (and amount)(CaSt is calcium stearate, Aldi-St is aluminum distearate, MgAc is magneesium acetate, with like labels for others salts tested) as listed:

THERMOPLASTIC ARTICLE FORMULATION TABLE

| Example # | Polymer Type | Silver-Containing Agent | Carboxylic Acid Salt (in ppm) |
|---|---|---|---|
| 1 | PP | RC-5000 (10000 ppm) | MgSt (3000 ppm) |
| 2 | PP | RC-5000 (10000 ppm) | CaSt (3000 ppm) |
| 3 | PP | RC-5000 (10000 ppm) | BaSt (3000 ppm) |
| 4 | PP | RC-5000 (10000 ppm) | CdSt (3000 ppm) |
| 5 | PP | RC-5000 (10000 ppm) | Sn(II)St (3000 ppm) |
| 6 | PP | RC-2000 (10000 ppm) | MgSt (3000 ppm) |
| 7 | PP | RC-2000 (10000 ppm) | CaSt (3000 ppm) |
| 8 | PP | RC-2000 (10000 ppm) | BaSt (3000 ppm) |
| 9 | PP | RC-2000 (10000 ppm) | ZnSt (3000 ppm) |
| 10 | PP | RC-2000 (10000 ppm) | CdSt (3000 ppm) |
| 11 | PP | RC-2000 (10000 ppm) | Sn(II)St (3000 ppm) |
| 12 | PP | ZEOMIC (10000 ppm) | NaSt (3000 ppm) |
| 13 | PP | ZEOMIC (10000 ppm) | CaSt (3000 ppm) |
| 14 | PP | RC-5000 (10000 ppm) | LiSt (100 ppm) |
| 15 | PP | RC-5000 (10000 ppm) | MgSt (1000 ppm) |
| 16 | PP | RC-5000 (10000 ppm) | MgSt (2431 ppm) |
| 17 | PP | RC-5000 (10000 ppm) | MgSt (10000 ppm) |
| 18 | PP | RC-5000 (10000 ppm) | CaSt (1000 ppm) |
| 19 | PP | RC-5000 (10000 ppm) | CaSt (1514 ppm) |
| 20 | PP | RC-5000 (10000 ppm) | CaSt (10000 ppm) |
| 21 | PP | RC-5000 (10000 ppm) | BaSt (100 ppm) |
| 22 | PP | RC-5000 (10000 ppm) | BaSt (300 ppm) |
| 23 | PP | RC-5000 (10000 ppm) | BaSt (1000 ppm) |
| 24 | PP | RC-5000 (10000 ppm) | BaSt (10000 ppm) |
| 25 | PP | RC-5000 (10000 ppm) | CdSt (100 ppm) |
| 26 | PP | RC-5000 (10000 ppm) | CdSt (300 ppm) |
| 27 | PP | RC-5000 (10000 ppm) | CdSt (1000 ppm) |
| 28 | PP | RC-5000 (10000 ppm) | CdSt (10000 ppm) |
| 29 | PP | RC-5000 (10000 ppm) | Sn(II)St (100 ppm) |
| 30 | PP | RC-5000 (10000 ppm) | Sn(II)St (300 ppm) |
| 31 | PP | RC-5000 (10000 ppm) | Sn(II)St (1000 ppm) |
| 32 | PP | RC-5000 (10000 ppm) | AlSt (100 ppm) |
| 33 | PP | RC-5000 (10000 ppm) | AlSt (300 ppm) |
| 34 | PP | RC-5000 (10000 ppm) | AlSt (1000 ppm) |
| 35 | PP | RC-5000 (10000 ppm) | AlSt (3000 ppm) |
| 36 | PP | RC-5000 (10000 ppm) | Aldi-St (100 ppm) |
| 37 | PP | RC-5000 (10000 ppm) | Aldi-St (300 ppm) |
| 38 | PP | RC-5000 (10000 ppm) | Aldi-St (1000 ppm) |
| 39 | PP | RC-5000 (10000 ppm) | Aldi-St (3000 ppm) |
| 40 | PP | RC-5000 (10000 ppm) | Altri-St (100 ppm) |
| 41 | PP | RC-5000 (10000 ppm) | Altri-St (300 ppm) |
| 42 | PP | RC-5000 (10000 ppm) | Altri-St (1000 ppm) |
| 43 | PP | RC-5000 (10000 ppm) | Altri-St (3000 ppm) |
| 44 | HDPE | RC-5000 (10000 ppm) | LiSt (10000 ppm) |
| 45 | HDPE | RC-5000 (10000 ppm) | NaSt (3000 ppm) |
| 46 | HDPE | RC-5000 (10000 ppm) | NaSt (10000 ppm) |
| 47 | HDPE | RC-5000 (10000 ppm) | KSt (10000 ppm) |
| 48 | HDPE | RC-5000 (10000 ppm) | MgSt (3000 ppm) |
| 49 | HDPE | RC-5000 (10000 ppm) | MgSt (10000 ppm) |

-continued

THERMOPLASTIC ARTICLE FORMULATION TABLE

| Example # | Polymer Type | Silver-Containing Agent | Carboxylic Acid Salt (in ppm) |
|---|---|---|---|
| 50 | HDPE | RC-5000 (10000 ppm) | CaSt (3000 ppm) |
| 51 | HDPE | RC-5000 (10000 ppm) | CaSt (10000 ppm) |
| 52 | HDPE | RC-5000 (10000 ppm) | BaSt (3000 ppm) |
| 53 | HDPE | RC-5000 (10000 ppm) | BaSt (10000 ppm) |
| 54 | HDPE | RC-5000 (10000 ppm) | ZnSt (3000 ppm) |
| 55 | HDPE | RC-5000 (10000 ppm) | CdSt (3000 ppm) |
| 56 | HDPE | RC-5000 (10000 ppm) | Sn(II)St (3000 ppm) |
| 57 | LLDPE | RC-5000 (10000 ppm) | LiSt (3000 ppm) |
| 58 | LLDPE | RC-5000 (10000 ppm) | NaSt (3000 ppm) |
| 59 | LLDPE | RC-5000 (10000 ppm) | MgSt (3000 ppm) |
| 60 | LLDPE | RC-5000 (10000 ppm) | CaSt (3000 ppm) |
| 61 | LLDPE | RC-5000 (10000 ppm) | BaSt (3000 ppm) |
| 62 | LLDPE | RC-5000 (10000 ppm) | ZnSt (3000 ppm) |
| 63 | LLDPE | RC-5000 (10000 ppm) | CdSt (3000 ppm) |
| 64 | LLDPE | RC-5000 (10000 ppm) | Sn(II)St (3000 ppm) |
| 65 | PS | RC-5000 (10000 ppm) | CaSt (3000 ppm) |

Each article was produced after the initial polymer and additives were first blended in a Kenwood mixer for 5 minutes at low speed. All samples were then melt-compounded on a Killion single screw extruder at a ramped temperature from about 205° to 230° C. through four heating zones. The melt temperature upon exit of the extruder die was about 230° C. The screw had a diameter of 2.54 cm and a length/diameter ratio of 32:1. Upon melting the molten polymer was filtered through a 300 mesh (48 micron) screen (with an output of about 1 kilogram/10 minutes, about 115 rpm). The individual plaques of the target polypropylene, HDPE, LLDPE, and polystyrene were then made through molding in an Arburg 25 ton injection molder. The plaques had dimensions of about 50 mm×70 mm×1.00 mm (with surface area of about 0.71 $dm^2$), and were made in a mold having a polished mirror finish. The mold cooling circulating water was controlled at a temperature of about 30+/−1° C.

Analyses for Surface-Available Silver

Each article was then exposed to an extract solution at room temperature for 24 hours (or more, as listed below). In each instance below, the extract solution used was a sodium-potassium phosphate buffer solution, although any salt solution (e.g., sodium chloride, calcium chloride, and the like) could also be utilized as the test extract solution as long as proper silver extraction is permitted with such solutions. Controls with silver antimicrobial but no carboxylic acid salt were tested as comparisons.

The extraction procedure and analyses involved first producing a standard plot of different silver concentrations within a nitric acid solution. The silver preparations were prepared by first weighing out 1000 ppm of silver into 100 mL volumetric flask and adding 0.5 mL of a 5% nitric acid solution to the flask to the fill line (to produce a 1 ppm silver standard). A further dilution of 10 g of the 1 ppm preparation into a 100 mL volumetric flask and then adding the remainder of 5% nitric acid solution (to produce a 100 ppb standard. A final 500 ppb standard was then prepared in similar fashion with 5 g of the 100 ppb standard used. The concentrations were then measured by utilization of inductively coupled plasma spectroscopy for such silver content. The results were then plotted for comparison with the eventual silver content of the extract solutions below.

The extract solution a 1×strength solution of a sodium-potassium-phosphate solution (initially about 145 g of sodium phosphate mixed with about 71 g of potassium phosphate diluted in a 1 liter volumetric flask with deionized water, with a subsequent dilution of 100 mL of this first solution to 1000 mL with deionized water). The treated plaques were then individually placed within a sealed plastic bag with a sufficient amount of the extract solution to fully immerse the sample. The bag was then placed and placed on an orbital shaker at 140 rpm and kept at room temperature for 24 hours. After that time, 9.5 mL of the resultant extract solution was then placed into a 15 mL vial with 0.5% of 70% nitric acid added. The resultant test extract solution was then subjected to ICP spectroscopy and the resulting measurements of silver concentration were then plotted against the standards, above. The measurements for the above plaque samples are as follows:

EXPERIMENTAL SILVER EXTRACTION TABLE

| Example # | Amount of Silver Detected ($\mu g/dm^2$) |
|---|---|
| 1 | 0.25 |
| 2 | 0.33 |
| 3 | 0.29 |
| 4 | 0.52 |
| 5 | 0.32 |
| 6 | 0.90 |
| 7 | 1.10 |
| 8 | 0.92 |
| 9 | 0.78 |
| 10 | 0.92 |
| 11 | 0.63 |
| 12 | 0.82 |
| 13 | 0.90 |
| 14 | 0.19 |
| 15 | 0.22 |
| 16 | 0.23 |
| 17 | 0.21 |
| 18 | 0.26 |
| 19 | 0.34 |
| 20 | 0.50 |
| 21 | 0.25 |
| 22 | 0.27 |
| 23 | 0.22 |
| 24 | 0.32 |
| 25 | 0.26 |
| 26 | 0.25 |
| 27 | 0.33 |
| 28 | 0.41 |
| 29 | 0.21 |
| 30 | 0.23 |
| 31 | 0.25 |

EXPERIMENTAL SILVER EXTRACTION TABLE

| Example # | Amount of Silver Detected ($\mu g/dm^2$) |
|---|---|
| 32 | 0.22 |
| 33 | 0.21 |
| 34 | 0.26 |
| 35 | 0.25 |
| 36 | 0.27 |
| 37 | 0.26 |
| 38 | 0.30 |
| 39 | 0.27 |
| 40 | 0.29 |
| 41 | 0.25 |
| 42 | 0.26 |
| 43 | 0.25 |
| 44 | 0.23 |
| 45 | 0.30 |
| 46 | 0.33 |
| 47 | 0.40 |
| 48 | 0.54 |
| 49 | 0.31 |
| 50 | 0.81 |
| 51 | 0.73 |
| 52 | 0.36 |
| 53 | 0.31 |
| 54 | 0.57 |
| 55 | 0.70 |
| 56 | 0.44 |
| 57 | 0.31 |
| 58 | 0.29 |
| 59 | 0.37 |
| 60 | 0.85 |
| 61 | 0.34 |
| 62 | 0.45 |
| 63 | 0.52 |
| 64 | 0.26 |
| 65 | 1.09 |
| Control (PP) (RC-5000)(1%) | 0.17 |
| Control (PP) (RC-2000)(1%) | 0.69 |
| Control (PP) (ZEOMIC)(1%) | 0.58 |
| Control (HDPE) (RC-5000)(1%) | 0.22 |
| Control (LLDPE) (RC-5000)(1%) | 0.16 |
| Control (PS) (RC-5000)(1%) | 0.62 |

Thus, unexpectedly, in comparison with the controls, the inventive articles exhibit increases (in differing degrees) of available silver at the surfaces thereof, particularly in polyolefin for silver zirconium phosphate types (RC-5000, RC-2000) of at least 0.25 $\mu g/dm^2$, for silver zeolite of at least 0.75, and for styrenics any silver-containing antimicrobial of at least 0.80.

There are, of course, many alternative embodiments and modifications of the present invention which are intended to be included within the spirit and scope of the following claims.

What I claim is:

1. A polyolefin article comprising at least one silver-zirconium phosphate antimicrobial agent in an amount of at most 1% by weight of the total article and at least one carboxylic acid salt compound, wherein said article exhibits a surface-available amount of silver compound of at least 0.25 micrograms of silver/square decimeters of said surface, as measured by a salt-extraction test of 24 hours at room temperature.

2. A polyolefin article comprising at least one silver zeolite antimicrobial agent in an amount of at most 1% by weight of the total article and at least one carboxylic salt compound, wherein said article exhibits a surface-available amount of silver compound of at least 0.75 micrograms of silver/square decimeters of said surface, as measured by a salt-extraction test of 24 hours at room temperature.

* * * * *